United States Patent [19]

Rentzea et al.

[11] Patent Number: 5,192,358
[45] Date of Patent: Mar. 9, 1993

[54] OXALIC ACID DERIVATIVES, THEIR PREPARATION AND PLANT GROWTH REGULATORS CONTAINING THEM

[75] Inventors: Costin Rentzea, Heidelberg; Wilhelm Rademacher, Limburgerhof, both of Fed. Rep. of Germany

[73] Assignee: BASF Aktiengesellschaft, Ludwigshafen, Fed. Rep. of Germany

[21] Appl. No.: 723,872

[22] Filed: Jul. 1, 1991

[30] Foreign Application Priority Data

Jul. 12, 1990 [DE] Fed. Rep. of Germany ....... 4022265

[51] Int. Cl.$^5$ .................. A01N 37/44; C07C 229/00; C07C 69/74
[52] U.S. Cl. .................................. 504/307; 560/39; 560/41; 560/116; 560/125; 560/155; 562/597; 504/315; 504/319; 504/312; 504/182; 504/190; 504/186; 504/171
[58] Field of Search ................... 560/39, 41, 155, 116, 560/125; 562/597; 71/111

[56] References Cited

FOREIGN PATENT DOCUMENTS 2002021 5/1990 Canada .

OTHER PUBLICATIONS

Plant Growth Regulating Chemicals—Cereal Grains, vol. 1, pp. 253–271 (1983) Jung et al.

Corn Production, Irrigation and Plant Growth Regulators, pp. 103–109 (1987) Shanahan et al.

*Primary Examiner*—Paul J. Killos
*Assistant Examiner*—Joseph M. Conrad
*Attorney, Agent, or Firm*—Keil & Weinkauf

[57] ABSTRACT

Oxalylhydroxamic acid derivatives of the formula I $$R^1-ON(R^2)-CO-CO-X-R^3 \qquad I,$$

where the substituents have the following meanings:
X is oxygen or sulfur;
$R^1$ is
  substituted or unsubstituted alkyl, alkenyl or alkynyl;
  substituted or unsubstituted monocyclic or polycyclic cycloalkyl or cycloalkylmethyl;
  substituted or unsubstituted phenyl or phenyl-$C_1$–$C_4$-alkyl;
$R^2$ is hydrogen or alkyl;
$R^3$ is
  substituted or unsubstituted alkyl, alkenyl or alkynyl;
  substituted or unsubstituted monocyclic or polycyclic cycloalkyl;
  substituted or unsubstituted phenyl-$C_1$–$C_4$-alkyl or phenoxy-$C_1$–$C_4$-alkyl;

and their agriculturally useful salts; their manufacture; growth-regulating agents containing them; and methods of regulating plant growth.

5 Claims, No Drawings

OXALIC ACID DERIVATIVES, THEIR PREPARATION AND PLANT GROWTH REGULATORS CONTAINING THEM

The present invention relates to oxalylhydroxamic acid derivatives of the general formula I $$R^1-ON(R^2)-CO-CO-X-R^3 \quad \text{I}$$

where

X is oxygen or sulfur;

$R^1$ is $C_3-C_{18}$-alkenyl or $C_3-C_8$-alkynyl, where these groups may carry from one to five halogen atoms, monocyclic or polycyclic $C_3-C_{10}$-cycloalkyl or $C_3-C_{10}$-cycloalkylmethyl, where these rings may carry from one to three $C_1-C_4$-alkyl groups and/or one phenyl ring, or phenyl, where the aromatic radical may carry from one to five halogen atoms and/or from one to three of the following groups: nitro, $C_1-C_4$-alkyl, $C_1-C_4$-haloalkyl, $C_1-C_4$-alkoxy, $C_1-C_4$-haloalkoxy, $C_1-C_4$-alkylthio or $C_1-C_4$-haloalkylthio;

$R^2$ is hydrogen, $C_1-C_4$-alkyl, $C_3$- or $C_4$-alkenyl or benzyl, where the aromatic radical may carry from one to five halogen atoms and/or from one to three of the following groups: $C_1-C_4$-alkyl, $C_1-C_4$-haloalkyl, $C_1-C_4$-alkoxy, $C_1-C_4$-haloalkoxy, $C_1-C_4$-alkylthio or $C_1-C_4$-haloalkylthio;

$R^3$ is $C_1-C_{20}$-alkyl which may carry from one to five halogen atoms and/or from one to three of the following groups: cyano, $C_1-C_{10}$-alkoxy, $C_1-C_4$-haloalkoxy, $C_1-C_4$-alkylthio, $C_1-C_4$-haloalkylthio, $C_3-C_{10}$-cycloalkyl, $C_3-C_{10}$-cycloalkoxy, $C_3-C_{10}$-cycloalkylthio or $C_3-C_{12}$-alkenyloxy, $C_3-C_{18}$-alkenyl or $C_3-C_{18}$-alkynyl, where these groups may carry from one to five halogen atoms, monocyclic or polycyclic $C_3-C_{10}$-cycloalkyl which may carry from one to three $C_1-C_4$-alkyl groups, or phenyl-$C_1-C_4$-alkyl or phenoxy-$C_1-C_4$-alkyl, where the aromatic radicals may carry from one to five halogen atoms and/or from one to three of the following groups: nitro, $C_1-C_4$-alkyl, $C_1-C_4$-haloalkyl, $C_1-C_4$-alkoxy, $C_1-C_4$-haloalkoxy, $C_1-C_4$-alkylthio or $C_1-C_4$-haloalkylthio, and their agriculturally useful salts.

The present invention furthermore relates to processes for the preparation of these compounds, agents containing them and methods for using oxalylhydroxamic acid derivatives of the general formula IA

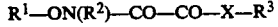

where

X is oxygen or sulfur;

$R^1$ is $C_1-C_{20}$-alkyl, $C_3-C_{18}$-alkenyl or $C_3-C_8$-alkynyl, where these groups may carry from one to five halogen atoms, $C_2-C_8$-alkyl which carries a $C_1-C_{12}$-alkoxy group, monocyclic or polycyclic $C_3-C_{10}$-cycloalkyl or $C_3-C_{10}$-cycloalkylmethyl, where these rings may carry from one to three $C_1-C_4$-alkyl groups and/or one phenyl ring, or phenyl or phenyl-$C_1-C_4$-alkyl, where the aromatic radicals may carry from one to five halogen atoms and/or from one to three of the following groups: nitro, $C_1-C_4$-alkyl, $C_1-C_4$-haloalkyl, $C_1-C_4$-alkoxy, $C_1-C_4$-haloalkoxy, $C_1-C_4$-alkylthio or $C_1-C_4$-haloalkylthio;

$R^2$ is hydrogen, $C_1-C_4$-alkyl, $C_3$- or $C_4$-alkenyl or benzyl, where the aromatic radical may carry from one to five halogen atoms and/or from one to three of the following groups: $C_1-C_4$-alkyl, $C_1-C_4$-haloalkyl, $C_1-C_4$-alkoxy, $C_1-C_4$-haloalkoxy, $C_1-C_4$-alkylthio or $C_1-C_4$-haloalkylthio;

$R^3$ is $C_1-C_{20}$-alkyl which may carry from one to five halogen atoms and/or from one to three of the following groups: cyano, $C_1-C_{10}$-alkoxy, $C_1-C_4$-haloalkoxy, $C_1-C_4$-alkylthio, $C_1-C_4$-haloalkylthio, $C_3-C_{10}$-cycloalkyl, $C_3-C_{10}$-cycloalkoxy, $C_3-C_{10}$-cycloalkylthio or $C_3-C_{12}$-alkenyloxy, $C_3-C_{18}$-alkenyl or $C_3-C_8$-alkynyl, where these groups may carry from one to five halogen atoms, monocyclic or polycyclic $C_3-C_{10}$-cycloalkyl which may carry from one to three $C_1-C_4$-alkyl groups, or phenyl-$C_1-C_4$-alkyl or phenoxy-$C_1-C_4$-alkyl, where the aromatic radicals may carry from one to five halogen atoms and/or from one to three of the following groups: nitro, $C_1-C_4$-alkyl, $C_1-C_4$-haloalkyl, $C_1-C_4$-alkoxy, $C_1-C_4$-haloalkoxy, $C_1-C_4$-alkylthio or $C_1-C_4$-haloalkylthio, as plant growth regulators.

Oxalylhydroxamic acid derivatives are disclosed in the literature as intermediates for syntheses. For example, ethyl (methoxyamino)-oxoacetate, ethyl (ethoxyamino)-oxoacetate, ethyl (isopropoxyamino)-oxoacetate and ethyl (benzyloxyamino)-oxoacetate are disclosed in the technical literature (cf. for example M. Takebayashi et al., Bull. Chem. Soc. Japan 45 (1972), 3567, and D. Geffken et al., Chemiker Zeitg. 109 (1985), 190).

CA-A 2,002,021 also describes the microbicidal and herbicidal action of oxalylhydroxamic acid derivatives whose general formula encompasses compounds I defined above. However, a growth-regulating action of such compounds has hitherto not been disclosed.

It is an object of the present invention to provide novel active herbicides and plant growth regulators.

We have found that this object is achieved by the oxalylhydroxamic acid derivatives I defined at the outset.

We have also found processes for the preparation of these oxalylhydroxamic derivatives, agents containing them and methods for using the oxalylhydroxamic derivatives IA, which are likewise defined at the outset.

The oxalylhydroxamic acid derivatives I are obtainable by various methods. They are particularly advantageously obtained by one of the processes A or B described below.

Process A

The oxalylhydroxamic acid derivatives of the formula I are obtained, for example, by reacting an oxalyl ester halide of the general formula II with a hydroxylamine of the general formula III in a conventional manner in an inert organic solvent in the presence of a base.

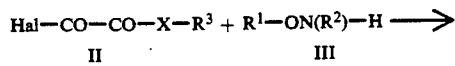

-continued

In the formula II, Hal is halogen, such as fluorine, chlorine, bromine or iodine, preferably chlorine or bromine.

The reaction is carried out in general at from −20° to 120° C., preferably from 0° to 80° C.

Examples of suitable solvents are halohydrocarbons, in particular chlorohydrocarbons, e.g. 1,1,2,2-tetrachloroethylene or 1,1,2,2-tetrachloroethane, dichloropropane, methylene chloride, dichlorobutane, chloroform, chloronaphthalene, dichloronaphthalene, carbon tetrachloride, 1,1,1- or 1,1,2-trichloroethane, trichloroethylene, pentachloroethane, o-, m- or p-difluorobenzene, 1,2-dichloroethane, 1,1-dichloroethane, 1,2-cis-dichloroethylene, chlorobenzene, fluorobenzene, bromobenzene, iodobenzene, o-, m- or p-dichlorobenzene, o-, p- or m-dibromobenzene, o-, m- or p-chlorotoluene, or 1,2,4-trichlorobenzene; ethers, e.g. ethyl propyl ether, methyl tert-butyl ether, n-butyl ethyl ether, di-n-butyl ether, diisobutyl ether, diisoamyl ether, diisopropyl ether, anisole, phenetole, cyclohexyl methyl ether, diethyl ether, ethylene glycol dimethyl ether, tetrahydrofuran, dioxane or thioanisole; nitrohydrocarbons, such as nitromethane, nitroethane, nitrobenzene, o-, m-or p-chloronitrobenzene or o-nitrotoluene; nitriles, such as acetonitrile, butyronitrile, isobutyronitrile, benzonitrile, m-chlorobenzonitrile; aliphatic or cycloaliphatic hydrocarbons, e.g. heptane, pinane, nonane, o-, m- or p-cymene, gasoline fractions boiling within a range from 70° to 190° C., cyclohexane, methylcyclohexane, decalin, petroleum ether, hexane, naphtha, 2,2,4-trimethylpentane, 2,2,3-trimethylpentane, 2,3,3-trimethylpentane or octane; esters, such as e.g. ethyl acetate, ethyl acetoacetate or isobutyl acetate, amides, e.g. formamide, methylformamide or dimethylformamide; ketones, e.g. acetone or methyl ethyl ketone, and, if necessary also water and corresponding mixtures. It is also possible to use the compound of the formula III in excess as the solvent.

The solvent is advantageously used in an amount of from 100 to 2,000, preferably from 200 to 700, % by weight, based on starting material II.

Examples of suitable bases are potassium hydroxide, sodium hydroxide, potassium carbonate, sodium carbonate, lithium hydroxide, lithium carbonate, sodium bicarbonate, potassium bicarbonate, calcium hydroxide, calcium oxide, barium oxide, magnesium hydroxide, magnesium oxide, barium hydroxide, calcium carbonate, magnesium carbonate, magnesium bicarbonate, magnesium acetate, zinc hydroxide, zinc oxide, zinc carbonate, zinc bicarbonate, zinc acetate, sodium formate, sodium acetate, trimethylamine, triethylamine, tripropylamine, triisopropylamine, tributylamine, triisobutylamine, trisec-butylamine, tri-tert-butylamine, tribenzylamine, tricyclohexylamine, triamylamine, trihexylamine, N,N-dimethylaniline, N,N-diethylaniline, N,N-dipropylaniline, N,N-dimethyltoluidine, N,N-diethyltoluidine, N,N-dipropyltoluidine, N,N-dimethyl-4-aminopyridine, N,N-diethyl-4-aminopyridine, N,N-dipropyl-4-aminopyridine, N-methylpyrrolidine, N-ethylpyrrolidine, N-methylpiperidine, N-ethylpiperidine, N-methylimidazole, N-ethylimidazole, N-methylmorpholine, N-ethylmorpholine, N-methylhexamethyleneimine, N-ethylhexamethyleneimine, pyridine, quinoline, alpha-picoline, beta-picoline, isoquinoline, pyrimidine, acridine, N,N,N',N'-tetramethylethylenediamine, N,N,N',N'-tetraethylethylenediamine, quinoxaline, N-propyldiisopropylamine, N,N-dimethylcyclohexylamine, 2,6-lutidine, 2,4-lutidine, trifurfurylamine or triethylenediamine.

Process B

The compounds of the formula I are also obtained, for example, by first reacting an oxalylhydroxylamine of the general formula IV with an alkylating agent of the formula V in a conventional manner in an inert organic solvent and, where $R^2$ is not hydrogen, reacting the resulting oxalylhydroxamic acid derivative Ia with an alkylating agent of the general formula VI in a conventional manner in an inert organic solvent.

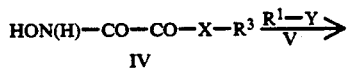

IV

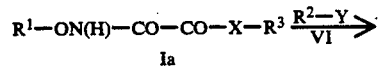

Ia

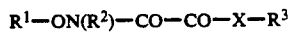

In the formulae V and VI, Y is a nucleophilically displaceable leaving group, such as halogen, e.g. chlorine, bromine or iodine, or alkyl- or arylsulfonyl, such as p-toluenesulfonyl.

The reaction is carried out in general at from −10° to 100° C., preferably from 0° to 80° C.

Examples of suitable solvents are those stated above for Process A. The following are particularly suitable: toluene, acetone, methyl ethyl ketone, dioxane, tetrahydrofuran, diethyl ether, methylene chloride, 1,1,1-trichloroethane and dimethylformamide.

Suitable bases in this process, in addition to those stated above, are lithium hydride and sodium hydride.

In view of the intended use of the compounds IA, suitable substituents are the following radicals:

X is oxygen or sulfur, preferably oxygen;

$R^1$ is $C_1$–$C_{20}$-alkyl, preferably branched or straight-chain $C_1$–$C_4$-alkyl, such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl, preferably branched or straight-chain $C_1$–$C_4$-alkyl, such as methyl, ethyl, propyl, 1-methylethyl, butyl, 1-methylpropyl, 2-methylpropyl or 1,1-dimethylethyl, $C_3$–$C_{18}$-alkenyl, in particular $C_3$–$C_6$-alkenyl, such as 2-propenyl, 2-butenyl, 3-butenyl, 1-methyl-2-propenyl, 2-methyl-2-propenyl, 2-pentenyl, 3-pentenyl, 4-pentenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-2-propenyl, 1-ethyl-2-propenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 1- methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-2-butenyl, 1,2-dimethyl-3-butenyl, 1,3-dimethyl-2-butenyl, 1,3-dimethyl-3-butenyl, 2,2-dimethyl-3-butenyl, 2,3-dimethyl-2-butenyl, 2,3-dimethyl-3-butenyl, 3,3-dimethyl-2-butenyl, 1-ethyl-2-butenyl, 1-ethyl-3-butenyl, 2-ethyl-2-butenyl, 2-ethyl-3-butenyl, 1,1,2-trimethyl-2-propenyl, 1-ethyl-1-methyl-2-propenyl or 1-ethyl-2-methyl-2-propenyl, preferably 2-propenyl, 2-butenyl or 2-methyl-2-propenyl, in particular 2-propenyl or 2-methyl-2-propenyl, or $C_3$–$C_8$-alkynyl, preferably $C_3$–$C_6$-alkynyl, such as 2-propynyl, 2-butynyl, 3-butynyl, 1-methyl-2-propynyl, 2-pentynyl, 3-pentynyl, 4-pentynyl, 1-methyl-2-butynyl, 1-methyl-3-butynyl, 2-methyl-3-butytnyl, 1,1-dimethyl-2-propynyl, 1-ethyl-2-propynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-4-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 1-ethyl-2-butynyl, 1-ethyl-3-butynyl, 2-ethyl-3-butynyl or 1-ethyl-1-methyl-2-propynyl, preferably 2-propynyl or 2-butynyl, where these groups may carry from one to five halogen atoms, such as fluorine, chlorine, bromine or iodine, preferably fluorine, chlorine or bromine, in particular chlorine or bromine, $C_2$–$C_8$-alkyl, in particular $C_2$–$C_6$-alkyl as stated above, which carries a $C_1$–$C_{12}$-alkoxy group, preferably a $C_1$–$C_8$-alkoxy group, in particular a $C_1$–$C_6$-alkoxy group, such as methoxy, ethoxy, propoxy, 1-methylethoxy, butoxy, 1-methylpropoxy, 2-methylpropoxy, 1,1-dimethylethoxy, pentyloxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, hexyloxy, 1-methylpentyloxy, 2-methylpentyloxy, 3-methylpentyloxy, 4-methylpentyloxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy or 1-methyl-2-methylpropoxy, monocyclic or polycyclic $C_3$–$C_{10}$-cycloalkyl, such as cyclopropyl, cyclobutyl, cyclopentyl, cyclohexyl, cycloheptyl, cyclooctyl, menthyl, norbornyl, adamantyl or tricyclodecanyl, preferably cyclopropyl, cyclopentyl or cyclohexyl, in particular cyclohexyl, or monocyclic or polycyclic $C_3$–$C_{10}$-cycloalkylmethyl, such as cyclopropylmethyl, cyclobutylmethyl, cyclopentylmethyl, cyclohexylmethyl, cycloheptylmethyl or cyclooctylmethyl, preferably cyclopropylmethyl, cyclopentylmethyl or cyclohexylmethyl, in particular cyclohexylmethyl, where these rings may carry from one to three $C_1$–$C_4$-alkyl groups, such as methyl, ethyl, propyl, 1-methylethyl, butyl, 1-methylpropyl, 2-methylpropyl or 1,1-dimethylethyl, preferably methyl, ethyl or 1-methylethyl, in particular methyl, and/or one phenyl ring, phenyl or phenyl-$C_1$–$C_4$-alkyl, such as benzyl, 1-phenylethyl, 2-phenylethyl, 1-phenylpropyl, 2-phenylpropyl, 3-phenylpropyl, 1-methyl-1-phenylethyl, 1-methyl-1-phenylethyl, 1-phenylbutyl, 2-phenylbutyl, 3-phenylbutyl, 4-phenylbutyl, 1-methyl-1-phenylpropyl, 1-methyl-2-phenylpropyl, 1-methyl-3-phenylpropyl, 2-methyl-1-phenylpropyl, 2-methyl-2-phenylpropyl, 2-methyl-3-phenylpropyl or 1,1-dimethyl-2-phenylethyl, where the aromatic radicals may carry from one to five halogen atoms, such as fluorine, chlorine, bromine or iodine, preferably fluorine, chlorine or bromine, and/or from one to three of the following groups: nitro, $C_1$–$C_4$-alkyl, such as methyl, ethyl, propyl, 1-methylethyl, butyl, 1-methylpropyl, 2-methylpropyl or 1,1-dimethylethyl, preferably methyl, ethyl, 1-methylethyl or 1,1-dimethylethyl, in particular methyl or ethyl, $C_1$–$C_4$-haloalkyl, in particular $C_1$- or $C_2$-haloalkyl, such as chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl or pentafluoroethyl, preferably trifluoromethyl, $C_1$–$C_4$-alkoxy, such as methoxy, ethoxy, propoxy, 1-methylethoxy, butoxy, 1-methylpropoxy, 2-methylpropoxy or 1,1-dimethylethoxy, preferably methoxy or ethoxy, $C_1$–$C_4$-haloalkoxy, in particular $C_1$- or $C_2$-haloalkoxy, such as chloromethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy or pentafluoroethoxy, preferably difluoromethoxy or trifluoromethoxy, $C_1$–$C_4$-alkylthio, such as methylthio, ethylthio, propylthio, 1-methylethylthio, butylthio, 1-methylpropylthio, 2-methylpropylthio or 1,1-dimethylethylthio, preferably methylthio, ethylthio, propylthio, butylthio or 2-methylpropylthio, or $C_1$–$C_4$-haloalkylthio, in particular $C_1$- or $C_2$-haloalkylthio, such as chloromethylthio, dichloromethylthio, trichloromethyltho, fluoromethylthio, difluoromethylthio, trifluoromethylthio, chlorofluoromethylthio, dichlorofluoromethylthio, chlorodifluoromethylthio, 1-fluoroethylthio, 2-fluoroethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, 2,2,2-trichloroethylthio or pentafluoroethylthio;

$R^2$ is hydrogen, $C_1$–$C_4$-alkyl, such as methyl, ethyl, propyl, 1-methylethyl, butyl, 1-methylpropyl, 2-methylpropyl or 1,1-dimethylethyl, preferably methyl or ethyl;

$C_3$- or $C_4$-alkenyl, such as 2-propenyl, 2-butenyl, 3-butenyl, 1-methyl-2-propenyl or 2-methyl-2-propenyl or benzyl, where the aromatic radical may carry from one to five halogen atoms, such as fluorine, chlorine, bromine or iodine, preferably fluorine, chlorine or bromine, and/or from one to three of the following groups: $C_1$–$C_4$-alkyl, such as methyl, ethyl, propyl, 1-methylethyl, butyl, 1-methylpropyl, 2-methylpropyl or 1,1-dimethylethyl, preferably methyl, ethyl, 1-methylethyl or 1,1-dimethylethyl, in particular methyl or ethyl, $C_1$–$C_4$-haloalkyl, in particular $C_1$- or $C_2$-haloalkyl, such as chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl or pentafluoroethyl, $C_1$–$C_4$-alkoxy, such as methoxy, ethoxy, propoxy, 1-methylethoxy, butyoxy, 1-methylpropoxy, 2-methylpropoxy or 1,1-dimethylethoxy, $C_1$–$C_4$-haloalkoxy, in particular $C_1$- or $C_2$-haloalkoxy, such as chloromethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy or pentafluoroethoxy, $C_1$–$C_4$-alkylthio, such as methylthio, ethylthio, propylthio, 1-methylethylthio, butylthio, 1-methylpropylthio, 2-methylpropylthio or 1,1-dimethylethylthio, or $C_1$–$C_4$-haloalkylthio, in particular $C_1$- or $C_2$-haloalkylthio, such as chloromethylthio, dichloromethylthio, trichloromethylthio, fluoromethylthio, difluoromethylthio, trifluoromethylthio, chlorofluoromethylthio, dichlorofluoromethylthio, chlorodifluoromethylthio, 1-fluoroethylthio, 2-fluoroethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, 2,2,2-trichloroethylthio or pentafluoroethylthio, and $R^3$ is $C_1$–$C_{20}$-alkyl, preferably branched or straight-chain $C_1$–$C_{16}$-alkyl, such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl, preferably straight-chain or branched $C_1$–$C_4$-alkyl, such as methyl, ethyl, propyl, 1-methylethyl, butyl, 1-methylpropyl, 2-methylpropyl or 1,1-dimethylethyl, octyl, 2-ethylhexyl, nonyl, decyl, dodecyl, tetradecyl or hexadecyl, which may carry from one to five halogen atoms, such as fluorine, chlorine, bromine or iodine, preferably fluorine, chlorine or bromine, in particular fluorine or chlorine, and/or from one to three of the following groups: cyano, $C_1$–$C_{10}$-alkoxy, such as methoxy, ethoxy, propoxy, 1-methylethoxy, butoxy, 1-methylpropoxy, 2-methylpropoxy, 1,1-dimethylethoxy, pentyloxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, hexyloxy, 1-methylpentyloxy, 2-methylpentyloxy, 3-methylpentyloxy, 4-methylpentyloxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy, 1-ethyl-2-methylpropoxy, heptyloxy, octyloxy, 2-ethylhexyloxy, nonyloxy or decyloxy, $C_1$–$C_4$-haloalkoxy, in particular $C_1$- or $C_2$-haloalkoxy, such as chloromethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy or pentafluoroethoxy, $C_1$–$C_4$-alkylthio, such as methylthio, ethylthio, propylthio, 1-methylethylthio, butylthio, 1-methylpropylthio, 2-methylpropylthio or 1,1-dimethylethylthio, preferably methylthio or ethylthio, $C_1$–$C_4$-haloalkylthio, in particular $C_1$- or $C_2$-haloalkylthio, such as chloromethylthio, dichloromethylthio, trichloromethylthio, fluoromethylthio, difluoromethylthio, trifluoromethylthio, chlorofluoromethylthio, dichlorofluoromethylthio, chlorodifluoromethylthio, 1-fluoroethylthio, 2-fluoroethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, 2,2,2-trichloroethylthio or pentafluoroethylthio, preferably trifluoromethylthio, $C_3$–$C_{10}$-cycloalkyl, such as cyclopropyl, cyclobutyl, cyclopentyl, cyclohexyl, cycloheptyl, cyclooctyl, menthyl, norbornyl, adamantyl or tricylcodecanyl, preferably cyclopropyl, cyclopentyl or cyclohexyl, $C_3$–$C_{10}$-cycloalkoxy, such as cyclopropoxy, cyclobutoxy, cyclopentyloxy, cyclohexyloxy, cycloheptyloxy, cyclooctyloxy, menthyloxy, norbornyloxy, adamantyloxy or tricyclodecanyloxy, preferably cyclopropoxy, cyclopentyloxy or cyclohexyloxy, $C_3$–$C_{10}$-cycloalkylthio, such as cyclopropylthio, cyclobutylthio, cyclopentylthio, cyclohexylthio, cycloheptylthio, cyclooctylthio, menthylthio, norbornylthio, adamantylthio or tricyclodecanylthio, preferably cyclohexylthio, or $C_3$–$C_{12}$-alkenyloxy, preferably $C_3$–$C_8$-alkenyloxy, in particular $C_3$–$C_6$-alkenyloxy, such as 2-propenyloxy, 2-butenyloxy, 3-butenyloxy, 1-methyl-2-propenyloxy, 2-methyl-2-propenyloxy, 2-pentenyloxy, 3-pentenyloxy, 4-pentenyloxy, 1-methyl-2-butenyloxy, 2-methyl-2-butenyloxy, 3-methyl-2-butenyloxy, 1 methyl-3-butenyloxy, 2-methyl-3-butenyloxy, 3-methyl-3-butenyloxy, 1,1-dimethyl-2-propenyloxy, 1,2-dimethyl-2-propenyloxy, 1-ethyl-2-propenyloxy, 2-hexenyloxy, 3-hexenyloxy, 4-hexenyloxy, 5-hexenyloxy, 1-methyl-2-pentenyloxy, 2-methyl-2-pentenyloxy, 3-methyl-2-pentenyloxy, 4-methyl-2-pentenyloxy, 1-methyl-3-pentenyloxy, 2-methyl-3-pentenyloxy, 3-methyl-3-pentenyloxy, 4-methyl-3-pentenyloxy, 1-methyl-4-pentenyloxy, 2-methyl-4-pentenyloxy, 3-methyl-4-pentenyloxy, 4-methyl-4-pentenyloxy, 1,1-dimethyl-2-butenyloxy, 1,2-dimethyl-2-butenyloxy, 1,3-dimethyl-2-butenyloxy, 2,3-dimethyl-2-butenyloxy, 1,1-dimethyl-3-butenyloxy, 1,2-dimethyl-3-butenyloxy, 1,3-dimethyl-3-butenyloxy, 2,2-dimethyl-3-butenyloxy, 2,3-dimethyl-3-butenyloxy, 1-ethyl-2-butenyloxy, 2- ethyl-2-butenyloxy, 1-ethyl-3-butenyloxy, 2-ethyl-3-butenyloxy, 1,1,2-trimethyl-2-propenyloxy, 1-ethyl-1-methyl-2-propenyloxy or 1-ethyl-2-methyl-2-propenyloxy; $C_3$–$C_{18}$-alkenyl, in particular $C_3$–$C_6$-alkenyl, such as 2-propenyl, 3-butenyl, 1-methyl-2-propenyl, 2-methyl-2-propenyl, 2-pentenyl, 3-pentenyl, 4-pentenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-2-propenyl, 1-ethyl-2-propenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-2-butenyl, 1,2-dimethyl-3-butenyl, 1,3-dimethyl-2-butenyl, 1,3-dimethyl-3-butenyl, 2,2-dimethyl-3-butenyl, 2,3-dimethyl-2-butenyl, 2,3-dimethyl-3-butenyl, 3,3-dimethyl-2-butenyl, 1-ethyl-2-butenyl, 1-ethyl-3-butenyl, 2-ethyl-2-butenyl, 2-ethyl-3-butenyl, 1,1,2-trimethyl-2-propenyl, 1-ethyl-1-methyl-2-propenyl or 1-ethyl-2-methyl-2-propenyl, preferably 2-propenyl, 2-butenyl or 2-methyl-2-propenyl or $C_3$–$C_8$-alkynyl, in particular $C_3$–$C_6$-alkynyl, such as 2-propynyl, 2-butynyl, 3-butynyl, 1-methyl-2-propynyl, 2-pentynyl, 3-pentynyl, 4-pentynyl, 1-methyl-2-butynyl, 1-methyl-3-butynyl, 2-methyl-3-butynyl, 1,1-dimethyl-2-propynyl, 1-ethyl-2-propynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-4-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 1-ethyl-2-butynyl, 1-ethyl-3-butynyl, 2-ethyl-3-butynyl or 1-ethyl-1-methyl-2-propynyl, preferably 2-propynyl, where these groups may carry from one to five halogen atoms, such as fluorine, chlorine, bromine or iodine, preferably fluorine, chlorine or bromine;

monocyclic or polycyclic $C_3$–$C_{10}$-cycloalkyl, such as cyclopropyl, cyclobutyl, cyclopentyl, cyclohexyl, cycloheptyl, cyclooctyl, menthyl, norbornyl, adamantyl or tricyclodecanyl, preferably cyclopropyl, cyclopentyl or cyclohexyl, which may carry from one to three $C_1$–$C_4$-alkyl groups, such as methyl, ethyl, propyl, 1-methylethyl, butyl, 1-methylpropyl, 2-methylpropyl or 1,1-dimethylethyl, preferably methyl, ethyl or 1-methylpropyl; phenyl-$C_1$–$C_4$-alkyl, such as benzyl, 1-phenylethyl, 2-phenylethyl, 1-phenylpropyl, 2-phenylpropyl, 3-phenylpropyl, 1-methyl-1-phenylethyl, 1-methyl-1-phenylethyl, 1-phenylbutyl, 2-phenylbutyl, 3-phenylbutyl, 4-phenylbutyl, 1-methyl-1-phenylpropyl, 1-methyl-2-phenylpropyl, 1-methyl-3-phenylpropyl, 2-methyl-1-phenylpropyl, 2-methyl-2-phenylpropyl, 2-methyl-3-phenylpropyl or 1,1-dimethyl-2-phenylethyl, preferably benzyl, 2-phenylethyl or 3-phenylpropyl, or phenoxy-$C_1$–$C_4$-alkyl, such as phenoxymethyl, 1-phenoxyethyl, 2-phenoxyethyl, 1-phenoxypropyl, 2-phenoxypropyl, 3-phenoxypropyl, 1-methyl-1-phenoxyethyl, 1-methyl-1-phenoxyethyl, 1-phenoxybutyl, 2-phenoxybutyl, 3-phenoxybutyl, 4-phenoxybutyl, 1-methyl-1-phenoxypropyl, 1-methyl-2-phenoxypropyl, 1-methyl-3-phenoxypropyl, 2-methyl-1-phenoxypropyl, 2-methyl-2-phenoxypropyl, 2-methyl-3-phenoxypropyl or 1,1-dimethyl-2-phenoxyethyl, preferably 2-phenoxyethyl, where the aromatic radicals may carry from one to five halogen atoms, such as fluorine, chlorine or iodine, preferably fluorine, chlorine or bromine and/or from one to three of the following groups: nitro, $C_1$–$C_4$-alkyl, such as methyl, ethyl, propyl, 1-methylethyl, butyl, 1-methylpropyl, 2-methylpropyl or 1,1-dimethylethyl, preferably methyl, $C_1$–$C_4$-haloalkyl, in particular $C_1$- or $C_2$-haloalkyl, such as chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl or pentafluoroethyl, preferably trifluoromethyl, $C_1$–$C_4$-alkoxy, such as methoxy, ethoxy, propoxy, 1-methylethoxy, butoxy, 1-methylpropoxy, 2-methylpropoxy or 1,1-dimethylethoxy, preferably methoxy or ethoxy, $C_1$–$C_4$-haloalkoxy, in particular $C_1$- or $C_2$-haloalkoxy, such as chloromethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy or pentafluoroethoxy, preferably trifluoromethoxy or difluoromethoxy, $C_1$–$C_4$-alkylthio, such as methylthio, ethylthio, propylthio, 1-methylethylthio, butylthio, 1-methylpropylthio, 2-methylpropylthio or 1,1-dimethylethylthio, preferably methylthio, or $C_1$–$C_4$-haloalkylthio, in particular $C_1$- or $C_2$-haloalkylthio, such as chloromethylthio, dichloromethylthio, trichloromethylthio, fluoromethylthio, difluoromethylthio, trifluoromethylthio, chlorofluoromethylthio, dichlorofluoromethylthio, chlorodifluoromethylthio, 1-fluoroethylthio, 2-fluoroethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, 2,2,2-trichloroethylthio or pentafluoroethylthio, preferably 2,2,2-trichloroethylthio.

Preferred compounds of the formula IA are those in which $R^1$ has the following meanings:

$C_1$–$C_{20}$-alkyl as stated generally and specifically above;

$C_3$–$C_{18}$-alkenyl, as stated generally and specifically above;

or $C_3$–$C_8$-alkynyl, as stated generally and specifically above, it being possible for these groups to bear from one to five halogen atoms, as stated generally and specifically above.

Further, compounds of the general formula IA are preferred in which $R^3$ denotes one of the following radicals:

$C_1$–$C_{20}$-alkyl as stated generally and specifically above;

$C_3$–$C_{18}$-alkenyl, as stated generally and specifically above;

or C₃–C₈-alkynyl, as stated generally and specifically above, it being possible for these groups to bear from one to five halogen atoms, as stated generally and specifically above, or monocyclic or polycyclic $C_3$–$C_{10}$-cycloalkyl or $C_3$–$C_{10}$-cycloalkylmethyl, as stated generally and specifically above, which may bear from one to three $C_1$–$C_4$-alkyl groups, as stated generally and specifically above.

Further preferred compounds of the general formula IA are those in which $R^2$ is hydrogen or methyl, and compounds IA in which X is oxygen.

Particularly preferred compounds IA are those in which the substituents have the following meanings:
X is oxygen;
$R^1$ is $C_3$–$C_{18}$-alkenyl, as stated generally and specifically above, these groups being able to bear from one to five halogen atoms, as stated generally and specifically above;
$R^2$ is hydrogen or methyl, and
$R^3$ is $C_1$–$C_{20}$-alkyl, as stated generally and specifically above, $C_3$–$C_{18}$-alkenyl, as stated generally and specifically above, or $C_3$–$C_8$-alkynyl, as stated generally and specifically above, it being possible for these groups to bear from one to five halogen atoms, as stated generally and specifically above, or monocyclic or polycyclic $C_3$–$C_{10}$-cycloalkyl or $C_3$–$C_{10}$-cycloalkylmethyl, as stated generally and specifically above, which may bear from one to three $C_1$–$C_4$-alkyl groups, as stated generally and specifically above.

Suitable salts of the compounds of the formula IA are agriculturally useful salts, for example alkali metal salts, in particular the sodium or potassium salt, alkaline earth metal salts, in particular the calcium, magnesium or barium salt, the manganese, copper, zinc or iron salt and ammonium, phosphonium, sulfonium or sulfoxonium salts, for example ammonium salts, benzyltrialkylammonium salts, trialkylsulfonium salts or trialkylsulfoxonium salts.

Examples of preferred oxalylhydroxamic acid derivatives of the general formula IA are shown in the table below.

TABLE

| Compounds of the general formula IA | | | |
|---|---|---|---|
| $R^1$—ON($R^2$)—CO—CO—X—$R^3$ | | | IA |
| $R^1$ | $R^2$ | $R^3$ | X |
| $CH_3$ | $CH_3$ | $C_2H_5$ | O |
| $C_2H_5$ | $C_2H_5$ | $C_2H_5$ | O |
| $C_2H_5$ | $CH_3$ | $C_2H_5$ | O |
| $C_2H_5$ | $C_2H_5$ | $C_2H_5$ | S |
| $C_2H_5$ | $C_2H_5$ | n-$C_3H_7$ | O |
| $C_2H_5$ | $C_2H_5$ | $CH_3$ | O |
| n-$C_3H_7$ | n-$C_3H_7$ | $C_2H_5$ | O |
| n-$C_3H_7$ | n-$C_3H_7$ | $C_2H_5$ | S |
| $CH_3$ | $CH_3$ | n-$C_3H_7$ | O |
| $CH_3$ | $CH_3$ | n-$C_4H_9$ | O |
| $C_2H_5$ | $C_2H_5$ | n-$C_4H_9$ | O |
| $C_2H_5$ | $C_2H_5$ | i-$C_4H_9$ | O |
| $CH_3$ | $CH_3$ | n-$C_6H_{13}$ | O |
| Allyl | Allyl | n-$C_6H_{13}$ | O |
| $CH_3$ | $CH_3$ | $H(CH_2)_4CH(C_2H_5)CH_2$ | O |
| $C_2H_5$ | $C_2H_5$ | n-$C_8H_{17}$ | O |
| $CH_3$ | $CH_3$ | n-$C_8H_{17}$ | O |
| n-$C_3H_7$ | n-$C_3H_7$ | n-$C_8H_{17}$ | O |
| Allyl | Allyl | n-$C_8H_{17}$ | O |
| $CH_3$ | $CH_3$ | n-$C_9H_{19}$ | O |
| $CH_3$ | $CH_3$ | n-$C_{10}H_{21}$ | O |
| $C_2H_5$ | $C_2H_5$ | n-$C_{12}H_{25}$ | O |
| $C_2H_5$ | $C_2H_5$ | n-$C_{12}H_{25}$ | S |
| $CH_3$ | H | $CH_3$ | O |
| $C_2H_5$ | H | $CH_3$ | O |
| n-$C_3H_7$ | H | $CH_3$ | O |
| i-$C_3H_7$ | H | $CH_3$ | O |
| $CH_2=CHCH_2$ | H | $CH_3$ | O |
| n-$C_4H_9$ | H | $CH_3$ | O |
| sec.-$C_4H_9$ | H | $CH_3$ | O |
| tert.-$CC_4H_9$ | H | $CH_3$ | O |
| $CH_2CH=CHCH_3$ | H | $CH_3$ | O |
| $CH_2CH=CHCH_3$ | H | $CH_3$ | S |
| $CH_2C(CH_3)=CH_2$ | H | $CH_3$ | O |
| $H_2C=C(Cl)CH_2$ | H | $CH_3$ | O |
| $ClCH=CHCH_2$ | H | $CH_3$ | O |
| $H_2C=C(Br)CH_2$ | H | $CH_3$ | O |
| $(CH_3)_2C=CHCH_2$ | H | $CH_3$ | O |
| n-$C_6H_{13}$ | H | $CH_3$ | O |
| $(CH_3)_3CCH_2CH_2$ | H | $CH_3$ | O |
| n-$C_8H_{17}$ | H | $CH_3$ | O |
| $CH_3CH_2CH_2CH_2CH(C_2H_5)CH_2$ | H | $CH_3$ | O |
| n-$C_{14}H_{29}$ | H | $CH_3$ | O |
| Cyclopropylmethyl | H | $CH_3$ | O |
| Cyclopentyl | H | $CH_3$ | O |
| Cyclohexyl | H | $CH_3$ | O |
| 4-Methylcyclohexyl | H | $CH_3$ | O |
| Cyclohexylmethyl | H | $CH_3$ | O |
| 4-tert.-Butylcyclohexyl | H | $CH_3$ | O |
| n-$C_3H_7$ | H | $C_2H_5$ | O |
| n-$C_3H_7$ | H | $C_2H_5$ | S |

TABLE-continued

Compounds of the general formula IA $$R^1—ON(R^2)—CO—CO—X—R^3 \quad IA$$

| R¹ | R² | R³ | X |
|---|---|---|---|
| CH₂=CHCH₂ | H | C₂H₅ | O |
| CH₃CH=CHCH₂ | H | C₂H₅ | O |
| ClCH=CHCH₂ | H | C₂H₅ | O |
| CH₂=C(Cl)CH₂ | H | C₂H₅ | O |
| CH₂=C(Br)CH₂ | H | C₂H₅ | O |
| CH₂=C(CH₃)CH₂ | H | C₂H₅ | O |
| (CH₃)₂C=CHCH₂ | H | C₂H₅ | O |
| n-C₄H₉ | H | C₂H₅ | O |
| i-C₄H₉ | H | C₂H₅ | O |
| Cl—(CH₂)₃ | H | C₂H₅ | O |
| Cl—(CH₂)₄ | H | C₂H₅ | O |
| Br—(CH₂)₄ | H | C₂H₅ | O |
| Cl—(CH₂)₆ | H | C₂H₅ | O |
| n-C₁₀H₂₁ | H | C₂H₅ | O |
| n-C₁₆H₂₃ | H | C₂H₅ | O |
| CH₃ | H | n-C₃H₇ | O |
| C₂H₅ | H | n-C₃H₇ | O |
| n-C₃H₇ | H | n-C₃H₇ | O |
| n-C₃H₇ | H | n-C₃H₇ | O |
| i-C₃H₇ | H | n-C₃H₇ | O |
| CH₂=CHCH₂ | H | n-C₃H₇ | O |
| n-C₄H₉ | H | n-C₃H₇ | O |
| i-C₄H₉ | H | n-C₃H₇ | O |
| CH₃CH=CHCH₂ | H | n-C₃H₇ | O |
| CH₂=C(CH₃)CH₂ | H | n-C₃H₇ | O |
| CH₂=C(Cl)CH₂ | H | n-C₃H₇ | O |
| CH₂=C(Br)CH₂ | H | n-C₃H₇ | O |
| (CH₃)₂C=CHCH₂ | H | n-C₃H₇ | O |
| n-C₁₄H₂₉ | H | n-C₃H₇ | O |
| CH₃ | H | CH₂CH₂Cl | O |
| C₂H₅ | H | CH₂CH₂Cl | O |
| n-C₃H₇ | H | CH₂CH₂Cl | O |
| i-C₃H₇ | H | CH₂CH₂Cl | O |
| CH₂=CHCH₂ | H | CH₂CH₂Cl | O |
| n-C₄H₉ | H | CH₂CH₂Cl | O |
| i-C₄H₉ | H | CH₂CH₂Cl | O |
| CH₃CH=CHCH₂ | H | CH₂CH₂Cl | O |
| CH₂=C(CH₃)CH₂ | H | CH₂CH₂Cl | O |
| CH₂=C(Cl)CH₂ | H | CH₂CH₂Cl | O |
| CH₂=C(Br)CH₂ | H | CH₂CH₂Cl | O |
| Cl—(CH₂)₃ | H | CH₂CH₂Cl | O |
| CH₃ | H | n-C₄H₉ | O |
| CH₃ | H | n-C₄H₉ | S |
| C₂H₅ | H | n-C₄H₉ | O |
| n-C₃H₇ | H | n-C₄H₉ | O |
| i-C₃H₇ | H | n-C₄H₉ | O |
| CH₂=CHCH₂ | H | n-C₄H₉ | O |
| HC≡CCH₂ | H | n-C₄H₉ | O |
| n-C₄H₉ | H | n-C₄H₉ | O |
| sec.-C₄H₉ | H | n-C₄H₉ | O |
| tert.-C₄H₉ | H | n-C₄H₉ | O |
| CH₃CH=CHCH₂ | H | n-C₄H₉ | O |
| CH₂=C(CH₃)CH₂ | H | n-C₄H₉ | O |
| CH₂=C(Cl)CH₂ | H | n-C₄H₉ | O |
| CH₂=C(Br)CH₂ | H | n-C₄H₉ | O |
| (CH₃)₂C=CHCH₂ | H | n-C₄H₉ | O |
| Cyclopropyl | H | n-C₄H₉ | O |
| Cyclopropylmethyl | H | n-C₄H₉ | O |
| Cyclopentyl | H | n-C₄H₉ | O |
| Cyclohexyl | H | n-C₄H₉ | O |
| 2-Cyclohexenyl | H | n-C₄H₉ | O |
| Cyclohexylmethyl | H | n-C₄H₉ | O |
| 4-Methylcyclohexyl | H | n-C₄H₉ | O |
| 4-tert.-Butylcyclohexyl | H | n-C₄H₉ | O |
| 1-Decalyl | H | n-C₄H₉ | O |
| 2-Decalyl | H | n-C₄H₉ | O |
| 2-Norbornyl | H | n-C₄H₉ | O |
| C₆H₅CH₂ | H | n-C₄H₉ | O |
| 4-F—C₆H₄CH₂ | H | n-C₄H₉ | O |
| 4-Cl—C₆H₄CH₂ | H | n-C₄H₉ | O |
| 2-Cl—C₆H₄CH₂ | H | n-C₄H₉ | O |
| 3-Cl—C₆H₄CH₂ | H | n-C₄H₉ | O |
| 4-Br—C₆H₄CH₂ | H | n-C₄H₉ | O |
| 2,4-Cl₂—C₆H₃CH₂ | H | n-C₄H₉ | O |
| 3,4-Cl₂—C₆H₃CH₂ | H | n-C₄H₉ | O |
| 4-CH₃—C₆H₄CH₂ | H | n-C₄H₉ | O |
| 4-F₃C—C₆H₄CH₂ | H | n-C₄H₉ | O |
| 4-CH₃O—C₆H₄CH₂ | H | n-C₄H₉ | O |

TABLE-continued

| Compounds of the general formula IA | | | |
|---|---|---|---|
| $R^1$—ON($R^2$)—CO—CO—X—$R^3$ | | | IA |
| $R^1$ | $R^2$ | $R^3$ | X |
| 4-$O_2$N—$C_6H_4CH_2$ | H | n-$C_4H_9$ | O |
| 4-tert.-$C_4H_9$—$C_6H_4CH_2$ | H | n-$C_4H_9$ | O |
| $CH_3$ | H | i-$C_4H_9$ | O |
| $C_2H_5$ | H | i-$C_4H_9$ | O |
| n-$C_3H_7$ | H | i-$C_4H_9$ | O |
| i-$C_3H_7$ | H | i-$C_4H_9$ | O |
| $CH_2$=$CHCH_2$ | H | i-$C_4H_9$ | O |
| HC≡$CCH_2$ | H | i-$C_4H_9$ | O |
| $H_3CC$≡$CHCH_2$ | H | i-$C_4H_9$ | O |
| n-$C_4H_9$ | H | i-$C_4H_9$ | O |
| i-$C_4H_9$ | H | i-$C_4H_9$ | O |
| $CH_2$=$C(CH_3)CH_2$ | H | i-$C_4H_9$ | O |
| $CH_2$=$C(Cl)CH_2$ | H | i-$C_4H_9$ | O |
| $CH_2$=$C(Br)CH_2$ | H | i-$C_4H_9$ | O |
| $Cl(CH_2)_3$ | H | i-$C_4H_9$ | O |
| $CH_3OCH_2CH_2$ | H | i-$C_4H_9$ | O |
| $CH_3OCH_2CH_2CH_2$ | H | i-$C_4H_9$ | O |
| $C_2H_5OCH_2CH_2$ | H | i-$C_4H_9$ | O |
| n-$C_3H_7OCH_2CH_2$ | H | i-$C_4H_9$ | O |
| $C_2H_5$ | H | $CH_2$=$CHCH_2$ | O |
| n-$C_3H_7$ | H | $CH_2$=$CHCH_2$ | O |
| i-$C_3H_7$ | H | $CH_2$=$CHCH_2$ | O |
| $CH_2$=$CHCH_2$ | H | $CH_2$=$CHCH_2$ | O |
| $CH_2$=$C(CH_3)CH_2$ | H | $CH_2$=$CHCH_2$ | O |
| $C_2H_5$ | H | $CH_3CH$=$CHCH_2$ | O |
| n-$C_3H_7$ | H | $CH_3CH$=$CHCH_2$ | O |
| $CH_2$=$CHCH_2$ | H | $CH_3CH$=$CHCH_2$ | O |
| $CH_2$=$C(CH_3)CH_2$ | H | $CH_3CH$=$CHCH_2$ | O |
| $C_2H_5$ | H | $ClCH$=$CHCH_2$ | O |
| n-$C_3H_7$ | H | $ClCH$=$CHCH_2$ | O |
| $CH_2$=$CHCH_2$ | H | $ClCH$=$CHCH_2$ | O |
| $CH_2$=$C(CH_3)CH_2$ | H | $ClCH$=$CHCH_2$ | O |
| $C_2H_5$ | H | $(CH_3)_2C$=$CHCH_2$ | O |
| n-$C_3H_7$ | H | $(CH_3)_2C$=$CHCH_2$ | O |
| $CH_2$=$CHCH_2$ | H | $(CH_3)_2C$=$CHCH_2$ | O |
| $C_2H_5$ | H | $C_8H_{17}CH$=$CHCH_2$ | O |
| n-$C_3H_7$ | H | $C_8H_{17}CH$=$CHCH_2$ | O |
| $C_2H_5$ | H | $C_{10}H_{21}CH$=$CHCH_2$ | O |
| n-$C_3H_7$ | H | $C_{10}H_{21}CH$=$CHCH_2$ | O |
| $CH_3$ | H | n-$C_5H_{11}$ | O |
| $C_2H_5$ | H | n-$C_5H_{11}$ | O |
| n-$C_3H_7$ | H | n-$C_5H_{11}$ | O |
| i-$C_3H_7$ | H | n-$C_5H_{11}$ | O |
| n-$C_4H_9$ | H | n-$C_5H_{11}$ | O |
| $CH_2$=$CHCH_2$ | H | n-$C_5H_{11}$ | O |
| $CH_2$=$C(CH_3)CH_2$ | H | n-$C_5H_{11}$ | O |
| $CH_3$ | H | n-$C_6H_{13}$ | O |
| $C_2H_5$ | H | n-$C_6H_{13}$ | O |
| n-$C_3H_7$ | H | n-$C_6H_{13}$ | O |
| i-$C_3H_7$ | H | n-$C_6H_{13}$ | O |
| $CH_2$=$CHCH_2$ | H | n-$C_6H_{13}$ | O |
| HC≡$CCH_2$ | H | n-$C_6H_{13}$ | O |
| $CH_2$=$C(CH_3)CH_2$ | H | n-$C_6H_{13}$ | O |
| $C_2H_5$ | H | $CH_3(CH_2)_3CH(C_2H_5)CH_2$ | O |
| n-$C_3H_7$ | H | $CH_3(CH_2)_3CH(C_2H_5)CH_2$ | O |
| i-$C_3H_7$ | H | $CH_3(CH_2)_3CH(C_2H_5)CH_2$ | O |
| $CH_2$=$CHCH_2$ | H | $CH_3(CH_2)_3CH(C_2H_5)CH_2$ | O |
| $CH_2$=$C(CH_3)CH_2$ | H | $CH_3(CH_2)_3CH(C_2H_5)CH_2$ | O |
| n-$C_4H_9$ | H | $CH_3(CH_2)_3CH(C_2H_5)CH_2$ | O |
| $C_2H_5$ | H | n-$C_8H_{17}$ | O |
| $C_2H_5$ | H | n-$C_9H_{19}$ | O |
| $C_2H_5$ | H | n-$C_{10}H_{21}$ | O |
| n-$C_3H_7$ | H | n-$C_{10}H_{21}$ | O |
| i-$C_3H_7$ | H | n-$C_{10}H_{21}$ | O |
| $CH_2$=$CHCH_2$ | H | n-$C_{10}H_{21}$ | O |
| $CH_2$=$C(CH_3)CH_2$ | H | n-$C_{10}H_{21}$ | O |
| $C_2H_5$ | H | n-$C_{12}H_{25}$ | O |
| n-$C_3H_7$ | H | n-$C_{12}H_{25}$ | O |
| i-$C_3H_7$ | H | n-$C_{12}H_{25}$ | O |
| $CH_2$=$CHCH_2$ | H | n-$C_{12}H_{25}$ | O |
| $CH_2$=$C(CH_3)CH_2$ | H | n-$C_{12}H_{25}$ | O |
| n-$C_4H_9$ | H | n-$C_{12}H_{25}$ | O |
| $C_2H_5$ | H | n-$C_{14}H_{29}$ | O |
| n-$C_3H_7$ | H | n-$C_{14}H_{29}$ | O |
| i-$C_3H_7$ | H | n-$C_{14}H_{29}$ | O |
| $CH_2$=$CHCH_2$ | H | n-$C_{14}H_{29}$ | O |
| $CH_2$=$C(CH_3)CH_2$ | H | n-$C_{14}H_{29}$ | O |
| $C_2H_5$ | H | n-$C_{16}H_{33}$ | O |

TABLE-continued

Compounds of the general formula IA
$R^1$—ON($R^2$)—CO—CO—X—$R^3$     IA

| $R^1$ | $R^2$ | $R^3$ | X |
|---|---|---|---|
| n-$C_3H_7$ | H | n-$C_{16}H_{33}$ | O |
| i-$C_3H_7$ | H | n-$C_{16}H_{33}$ | O |
| $CH_2$=CHCH$_2$ | H | n-$C_{16}H_{33}$ | O |
| $CH_2$=C(CH$_3$)CH$_2$ | H | n-$C_{16}H_{33}$ | O |
| n-$C_4H_9$ | H | n-$C_{16}H_{33}$ | O |
| $C_2H_5$ | H | n-$C_{18}H_{37}$ | O |
| $CH_2$=CHCH$_2$ | H | n-$C_{18}H_{37}$ | O |
| $C_2H_5$ | H | n-$C_{20}H_{41}$ | O |
| $C_2H_5$ | H | n-$C_3H_7O(CH_2)_3$ | O |
| $C_2H_5$ | H | n-$C_3H_7O(CH_2)_4$ | O |
| $C_2H_5$ | H | n-$C_3H_7O(CH_2)_6$ | O |
| $C_2H_5$ | H | i-$C_3H_7O(CH_2)_2$ | O |
| $C_2H_5$ | H | i-$C_3H_7O(CH_2)_4$ | O |
| $C_2H_5$ | H | n-$C_4H_9O(CH_2)_4$ | O |
| $C_2H_5$ | H | n-$C_4H_9O(CH_2)_6$ | O |
| $C_2H_5$ | H | i-$C_4H_9O(CH_2)_6$ | O |
| $C_2H_5$ | H | i-$C_4H_9O(CH_2)_6$ | O |
| $C_2H_5$ | H | sec.-$C_4H_9O(CH_2)_4$ | O |
| $C_2H_5$ | H | $(CH_3)_3CCH_2O(CH_2)_4$ | O |
| $C_2H_5$ | H | $(CH_3)_3CCH_2CH_2O(CH_2)_4$ | O |
| $C_2H_5$ | H | n-$C_6H_{13}O(CH_2)_4$ | O |
| $C_2H_5$ | H | $(CH_3)_2CHCH_2CH(C_2H_5)CH_2O(CH_2)_4$ | O |
| $C_2H_5$ | H | n-$C_8H_{17}O(CH_2)_4$ | O |
| $C_2H_5$ | H | n-$C_9H_{19}O(CH_2)_4$ | O |
| $C_2H_5$ | H | n-$C_{10}H_{21}O(CH_2)_4$ | O |
| $C_2H_5$ | H | cyclo-$C_5H_9O(CH_2)_4$ | O |
| $C_2H_5$ | H | cyclo-$C_6H_{11}O(CH_2)_4$ | O |
| $C_2H_5$ | H | $CH_2$=CHCH$_2$O(CH$_2$)$_4$ | O |
| $C_2H_5$ | H | $CH_2$=C(CH$_3$)CH$_2$O(CH$_2$)$_4$ | O |
| $C_2H_5$ | H | $(CH_3)_2C$=CHCH$_2$O(CH$_2$)$_4$ | O |
| $C_2H_5$ | H | $C_6H_5CH_2$ | O |
| $C_2H_5$ | H | 4-F—$C_6H_5CH_2$ | O |
| $C_2H_5$ | H | 4Cl—$C_6H_5CH_2$ | O |
| $C_2H_5$ | H | 4Br$C_6H_5CH_2$ | O |
| $C_2H_5$ | H | 4CH$_3C_6H_5CH_2$ | O |
| $C_2H_5$ | H | 4-CH$_3$O—$C_6H_5CH_2$ | O |
| $C_2H_5$ | H | 4-F$_3$C—$C_6H_4CH_2$ | O |
| $C_2H_5$ | H | 4 O$_2$N—$C_6H_4CH_2$ | O |
| $C_2H_5$ | H | 4-tert.-$C_4H_9$—$C_6H_4CH_2$ | O |
| $C_2H_5$ | H | 2,4-Cl$_2$—$C_6H_3CH_2$ | O |
| $C_2H_5$ | H | Cyclopentyl | O |
| $C_2H_5$ | H | Cyclopentylmethyl | O |
| $C_2H_5$ | H | Cyclohexyl | O |
| $C_2H_5$ | H | Cyclohexylmethyl | O |
| $C_2H_5$ | H | 4-Methylcyclohexyl | O |
| $C_2H_5$ | H | 2-Methylcyclohexyl | O |
| $C_2H_5$ | H | 4-Isopropylcyclohexyl | O |
| $C_2H_5$ | H | 4-tert.-Butylcyclohexyl | O |
| $C_2H_5$ | H | 2-Norbornyl | O |
| $C_2H_5$ | H | 1-Decalyl | O |
| $C_2H_5$ | H | 2-Decalyl | O |
| $CH_3$ | H | $C_2H_5$ | O |
| $C_2H_5$ | H | $C_2H_5$ | O |
| i-$C_3H_7$ | H | $C_2H_5$ | O |
| $C_6H_5CH_2$ | H | $C_2H_5$ | O |

The growth-regulating active ingredients IA, or agents containing them, may be applied for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredients according to the invention as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as toluene, xylene, paraffin, tetrahydronaphthalene, alkylated naphthalenes and their derivatives, methanol, ethanol, propanol, butanol, cyclohexanol, cyclohexanone, chlorobenzene, isophorone, etc., and strongly polar solvents such as N,N-dimethylformamide, dimethyl sulfoxide, N-methylpyrrolidone, water, etc. are suitable.

Aqueous formulations may be prepared from emulsion concentrates, pastes, oil dispersions, wettable powders or water-dispersible granules by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of aromatic sulfonic acids, e.g., ligninsulfonic acid, phenolsulfonic acid, naphthalenesulfonic acid and dibutylnaphthalenesulfonic acid, and of fatty acids, alkyl and alkylaryl sulfonates, and alkyl, lauryl ether and fatty alcohol sulfates, and salts of sulfated hexadecanols, heptadecanols, and octadecanols, salts of fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acids, silica gels, silicates, talc, kaolin, attapulgus clay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain meals, bark meal, wood meal, and nutshell meal, cellulosic powders, etc.

The formulations contain from 0.1 to 95, and preferably 0.5 to 90, % by weight of active ingredient. The active ingredients are used in a purity of from 90 to 100, preferably 95 to 100, % (according to the NMR spectrum).

Examples of formulations are as follows:

I. 90 parts by weight of compound no. 32 is mixed with 10 parts by weight of N-methyl-alpha-pyrrolidone. A mixture is obtained which is suitable for application in the form of very fine drops.

II. 20 parts by weight of compound no. 17 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

III. 20 parts by weight of compound no. 46 is dissolved in a mixture consisting of 40 parts by weight of cyclohexanone, 30 parts by weight of isobutanol, 20 parts by weight of the adduct of 7 moles of ethylene oxide and 1 mole of isooctylphenol, and 10 parts by weight of the adduct of 40 moles of ethylene oxide and 1 mole of castor oil. By pouring the solution into 100,000 parts by weight of water and finely distributing it therein, an aqueous dispersion is obtained containing 0.02% by weight of the active ingredient.

IV. 20 parts by weight of compound no. 46 is dissolved in a mixture consisting of 25 parts by weight of cyclohexanone, 65 parts by weight of a mineral oil fraction having a boiling point between 210° and 280° C., and 10 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

V. 20 parts by weight of compound no. 17 is well mixed with 3 parts by weight of the sodium salt of diisobutylnaphthalene-alpha-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of the active ingredient.

VI. 3 parts by weight of compound no. 32 is intimately mixed with 97 parts by weight of particulate kaolin. A dust is obtained containing 3% by weight of the active ingredient.

VII. 30 parts by weight of compound no. 17 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 20 parts by weight of compound no. 46 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

IX. 95 parts by weight of compound no. 32 is mixed with 5 parts by weight of N-methyl-α-pyrrolidone. A solution is obtained which is suitable for application in the form of minute drops.

The growth-regulating active ingredients or the agents containing them may be applied pre- or postemergence. If certain crop plants tolerate the active ingredients less well, application techniques may be used in which the herbicidal agents are sprayed from suitable equipment in such a manner that the leaves of sensitive crop plants are if possible not touched, and the agents reach the soil or the unwanted plants growing beneath the crop plants (post-directed, lay-by treatment).

The application rates of active ingredient IA depend on the objective to be achieved, the time of the year, the plants to be combated and their growth stage, and are from 0.001 to 5.0, and preferably 0.1 to 3.0, kg of active ingredient per hectare.

The active ingredients IA may influence virtually all development stages of a plant, and are therefore used as growth regulators. The diversity of action of growth regulators depends especially on a) the type and variety of plant;
b) the time applied, with reference to the development stage of the plants and the time of the year;
c) the place and method of application (seed treatment, soil treatment, or application to foliage);
d) climatic factors, e.g., average temperature, amount of precipitation, sunshine and duration;
e) soil conditions (including fertilization);
f) the formulation of the active ingredient; and g) the concentration at which the active ingredient is applied.

A description of some of the various possibilities of using the growth regulators according to the invention in agriculture and horticulture is given below.

A. Vegetative plant growth can be inhibited to a considerable extent, a fact which is manifested particularly in a reduction in plant height. The treated plants thus have a compact habit; furthermore, the leaf color is darker.

Of advantage in practice is for example the reduction in grass growth on roadsides, hedges, canal embankments and on areas such as parks, sportsgrounds, fruit orchards, lawns and airfields, thus reducing expensive and time-consuming mowing.

A further feature of economic interest is the increase in the rigor of crops which tend to lodge, such as cereals, Indian corn, sunflowers and soybeans. The shortening and strengthening of the stem thus caused reduces or eliminates the danger of lodging under unfavorable weather conditions.

The use of growth regulators is also important for inhibiting plant height and changing the time of ripening in cotton. It is thus possible for this important crop to be harvested completely mechanically.

In fruit and other trees, pruning costs can be reduced with growth regulators. With growth regulators, it is also possible to break up the alternate breeding rhythm of fruit trees.

Growth regulators may also increase or inhibit lateral branching. This is of interest when, for instance in tobacco plants, it is desired to inhibit the formation of lateral shoots (suckers) in favor of leaf development.

With growth regulators, it is possible for instance in winter rape to considerably increase the resistance to freeze injury. On the one hand, upward growth and the development of a too luxuriant (and thus particularly frost-susceptible) leaf or plant mass are inhibited; on the other, the young rape plants are kept, in spite of favorable growth conditions, in the vegetative development stage before winter frosts begin. The danger of freeze injury is thus eliminated in plants which tend to lose prematurely their inhibition to bloom and pass into the generative phase. In other crops, too, e.g., winter cereals, it is advantageous if the plants are well tillered in the fall as a result of treatment with the compounds according to the invention, but enter winter with not too lush a growth. This is a preventive measure against increased susceptibility to freeze injury and—because of the relatively low leaf or plant mass—attack by various (especially fungus) diseases. The inhibition of vegetative growth also makes closer planting possible in numerous crops, which means an increase in yield, based on the area cropped.

B. Better yields both of plant parts and plant materials may be obtained with the novel agents. It is thus for instance possible to induce increased formation of buds, blossom, leaves, fruit, seed grains, roots and tubers, to increase the sugar content of sugarbeets, sugarcane and citrus fruit, to raise the protein content of cereals and soybeans, and to stimulate the increased formation of latex in rubber trees.

The compounds of the formula I may raise the yield by influencing plant metabolism or by promoting or inhibiting vegetative and/or generative plant growth.

C. It is also possible with growth regulators to shorten or lengthen growth stages and to accelerate or retard the ripening process in plant parts either before or after harvesting. A factor of economic interest is for example the facilitation of harvesting made possible by a chemical, temporally concentrated loosening (abscission) of the adherence of stalks to the branches of citrus fruit, olive trees, and other kinds of pomes, drupes and indehiscent fruit. The same mechanism, i.e., promotion of the formation of separation layers between fruit or leaf and stem of the plant, is also essential for a readily controllable defoliation of crop plants, e.g., cotton.

D. Further, transpiration in crop plants may be reduced with growth regulators. This is particularly important for plants growing in agricultural areas which are expensive to irrigate, e.g., in arid or semi-arid areas. Irrigation frequency can be reduced by using the compounds according to the invention, making for lower costs. As a result of the use of growth regulators, the water available can be better utilized, because, inter alia, the size of the stomata opening is reduced;
a thicker epidermis and cuticle are formed;
penetration of the soil by the roots is improved;
the micro-climate in the stand is favorably influenced by the more compact growth.

The active ingredients according to the invention may be applied not only to the seed (as a dressing), but also to the soil, i.e., via the roots, and—the method particularly preferred—to the foliage by spraying.

To increase the spectrum of action and to achieve synergistic effects, the compounds of the formula IA according to the invention may be mixed with each other, or mixed and applied together with numerous representatives of other herbicidal or growth-regulating active ingredient groups. Examples of suitable components are diazines, 4H-3,1-benzoxazine derivatives, benzothiadiazinones, 2,6-dinitroanilines, N-phenylcarbamates, thiolcarbamates, halocarboxylic acids, triazines, amides, ureas, diphenyl ethers, triazinones, uracils, benzofuran derivatives, quinolinecarboxylic acids, (hetero)-aryloxyphenoxypropionic acid derivatives (salts, esters, amides), etc.

It may also be useful to apply the compounds of the formula IA, either alone or in combination with other herbicides, in admixture with other crop protection agents, e.g., agents for combating pests or phytopathogenic fungi or bacteria. The compounds may also be mixed with solutions of mineral salts used to remedy nutritional or trace element deficiencies. Nonphytotoxic oils and oil concentrates may also be added.

SYNTHESIS EXAMPLES

The directions given in the examples below were employed, after appropriate modifications to the starting materials, to obtain further active ingredients IA. The compounds thus obtained are listed with their physical details in the table below.

EXAMPLE 1

Methyl [(methoxy)-methylamino]oxo-acetate

At 25° C., 149.2 g (1.53 mol) of O,N-dimethylhydoxylamine hydrochloride, 268.2 g (3.28 mol) of sodium acetate and 133.2 g (1.09 mol) of oxalic acid monomethyl ester chloride were added one after the other to 1,500 ml of acetic acid. After the mixture had been stirred for 12 hours at 25° C., it was suction filtered and the filtrate was evaporated down. 500 ml of ethyl acetate was added to the residue, and the whole was then washed with 50 ml of water, dried over $Na_2SO_4$, evaporated down under reduced pressure and fractionally distilled.

There was obtained 108.8 g (68% of theory) of the title compound as a colorless liquid; b.p. 82° C./1 mbar.

EXAMPLE 2

Methyl (allyloxyamino)-oxo-acetate 13.3 g (0.11 mol) of allyl bromide was added to a suspension of 13.8 g (0.1 mol) of potassium carbonate and 11.9 g (0.1 mol) of methyl (hydroxyamino)-oxo-acetate in 110 ml of dimethylformamide, and the mixture was stirred for 10 hours at 60° C. The mixture was suction filtered, the filtrate was evaporated down under reduced pressure, and the residue was dissolved in 250 ml of ethyl acetate and washed with three times 25 ml of water. Drying over $Na_2SO_4$ was followed by dissolution in ethyl acetate and concentration under reduced pressure, finally at 80° C. and 0.2 mbar.

There was obtained 11.6 g (73% of theory) of the title compound as a colorless oil; $n_D^{22}$ 1,4718.

TABLE 1

$R^1$—$ON(R^2)$—$CO$—$CO$—$X$—$R^3$     IA

| Ex. No. | $R^1$ | $R^2$ | $R^3$ | X | mp (°C.) bp. (°C./mbar) Refractive index $^1$H-NMR (δ in ppm)* |
|---|---|---|---|---|---|
| 3 | $CH_3$ | $CH_3$ | $C_2H_5$ | O | $n_D^{22}$ 1.4339 |
| 4 | $C_2H_5$ | $C_2H_5$ | $C_2H_5$ | O | $n_D^{22}$ 1.4335 |
| 5 | $C_2H_5$ | $C_2H_5$ | $n$-$C_3H_7$ | O | $n_D^{23}$ 1.4350 |
| 6 | $C_2H_5$ | $C_2H_5$ | $CH_3$ | O | $n_D^{22}$ 1.4301 |
| 7 | $CH_3$ | $CH_3$ | $n$-$C_3H_7$ | O | $n_D^{22}$ 1.4358 |
| 8 | $CH_3$ | $CH_3$ | $n$-$C_4H_9$ | O | $n_D^{22}$ 1.4383 |
| 9 | $CH_3$ | $CH_3$ | $n$-$C_6H_{13}$ | O | $n_D^{22}$ 1.4422 |
| 10 | $CH_3$ | $CH_3$ | $CH_3CH_2CH_2CH_2CH(C_2H_5)CH_2$ | O | $n_D^{22}$ 1.4466 |
| 11 | $CH_3$ | $CH_3$ | $n$-$C_8H_{17}$ | O | $n_D^{22}$ 1.4455 |
| 12 | $CH_3$ | $CH_3$ | $n$-$C_9H_{19}$ | O | $n_D^{22}$ 1.4457 |
| 13 | $CH_3$ | $CH_3$ | $n$-$C_{10}H_{21}$ | O | $n_D^{23}$ 1.4477 |
| 14 | $CH_3$ | H | $CH_3$ | O | $n_D^{22}$ 1.4547 |
| 15 | $C_2H_5$ | H | $CH_3$ | O | $n_D^{23}$ 1.4549 |
| 16 | $n$-$C_3H_7$ | H | $CH_3$ | O | $n_D^{23}$ 1.4542 |
| 17 | $i$-$C_3H_7$ | H | $CH_3$ | O | $n_D^{22}$ 1.4541 |
| 18 | $n$-$C_4H_9$ | H | $CH_3$ | O | 115–120/0.3 |
| 19 | tert.-$C_4H_9$ | H | $CH_3$ | O | 59–62 |
| 20 | $CH_2C(CH_3)$=$CH_2$ | H | $CH_3$ | O | $n_D^{23}$ 1.4776 |
| 21 | $H_2C$=$C(Cl)CH_2$ | H | $CH_3$ | O | 133–135/0.3 |
| 22 | $ClCH$=$CHCH_2$ | H | $CH_3$ | O | $n_D^{22}$ 1.4951 |
| 23 | $H_2C$=$C(Br)CH_2$ | H | $CH_3$ | O | 135–137/0.3 |
| 24 | $n$-$C_6H_{13}$ | H | $CH_3$ | O | $n_D^{22}$ 1.4581 |
| 25 | $n$-$C_3H_7$ | H | $C_2H_5$ | O | $n_D^{23}$ 1.4532 |
| 26 | $CH_2$=$C(CH_3)CH_2$ | H | $C_2H_5$ | O | $n_D^{23}$ 1.4718 |
| 27 | $CH_3$ | H | $n$-$C_3H_7$ | O | $n_D^{23}$ 1.4538 |
| 28 | $C_2H_5$ | H | $n$-$C_3H_7$ | O | $n_D^{23}$ 1.4538 |
| 29 | $CH_3$ | H | $n$-$C_4H_9$ | O | $n_D^{22}$ 1.4532 |
| 30 | $C_2H_5$ | H | $n$-$C_4H_9$ | O | $n_D^{22}$ 1.4524 |
| 31 | $n$-$C_3H_7$ | H | $n$-$C_4H_9$ | O | $n_D^{22}$ 1.4529 |
| 32 | $i$-$C_3H_7$ | H | $n$-$C_4H_9$ | O | $n_D^{22}$ 1.4522 |
| 33 | $CH_2$=$CHCH_2$ | H | $n$-$C_4H_9$ | O | $n_D^{22}$ 1.4639 |
| 34 | $HC$≡$C$—$CH_2$ | H | $n$-$C_4H_9$ | O | $n_D^{22}$ 1.4759 |
| 35 | $n$-$C_4H_9$ | H | $n$-$C_4H_9$ | O | $n_D^{22}$ 1.4548 |
| 36 | tert.-$C_4H_9$ | H | $n$-$C_4H_9$ | O | $n_D^{22}$ 1.4518 |
| 37 | $CH_3$—$CH$=$CH$—$CH_2$ | H | $n$-$C_4H_9$ | O | $n_D^{22}$ 1.4672 |
| 38 | $CH_2$=$C(CH_3)CH_2$ | H | $n$-$C_4H_9$ | O | $n_D^{22}$ 1.4671 |
| 39 | $CH_2$=$C(Cl)CH_2$ | H | $n$-$C_4H_9$ | O | $n_D^{22}$ 1.4812 |
| 40 | $CH_2$=$C(Br)CH_2$ | H | $n$-$C_4H_9$ | O | $n_D^{22}$ 1.4988 |
| 41 | $CH_3$ | H | $n$-$C_5H_{11}$ | O | $n_D^{22}$ 1.4549 |
| 42 | $C_2H_5$ | H | $n$-$C_5H_{11}$ | O | $n_D^{23}$ 1.4537 |
| 43 | $CH_2$=$C(CH_3)CH_2$ | H | $n$-$C_5H_{11}$ | O | $n_D^{22}$ 1.4555 |
| 44 | $CH_3$ | H | $n$-$C_6H_{13}$ | O | $n_D^{23}$ 1.4551 |
| 45 | $C_2H_5$ | H | $n$-$C_6H_{13}$ | O | $n_D^{23}$ 1.4539 |
| 46 | $CH_2$=$C(CH_3)$—$CH_2$ | H | $n$-$C_6H_{13}$ | O | $n_D^{23}$ 1.4665 |
| 47 | $C_2H_5$ | H | $CH_3CH_2CH_2CH_2CH(C_2H_5)CH_2$ | O | $n_D^{23}$ 1.4561 |
| 48 | $C_2H_5$ | H | $n$-$C_{10}H_{21}$ | O | $n_D^{23}$ 1.4565 |
| 49 | $C_2H_5$ | H | $n$-$C_{12}H_{25}$ | O | 38–40 |
| 50 | $CH_3$ | H | $C_2H_5$ | O | 90/0.1 |
| 51 | $C_2H_5$ | H | $C_2H_5$ | O | 151/15 |
| 52 | $C_6H_5CH_2$ | H | $C_2H_5$ | O | 85–87 |
| 53 | $CH_2$=$C(Br)CH_2$ | H | $C_2H_5$ | O | $n_D^{22}$ 1.5055 |
| 54 | $CH_2$=$CHCH_2$ | H | $C_2H_5$ | O | $n_D^{22}$ 1.4684 |
| 55 | $(CH_3)_2CHCH_2$ | H | $C_2H_5$ | O | $n_D^{22}$ 1.4515 |
| 56 | $(CH_3)_2CH$ | H | $n$-$C_3H_7$ | O | $n_D^{22}$ 1.4518 |
| 57 | $CH_2$=$CHCH_2$ | H | $n$-$C_3H_7$ | O | $n_D^{22}$ 1.4663 |
| 58 | $(CH_3)_2CHCH_2$ | H | $n$-$C_3H_7$ | O | $n_D^{22}$ 1.4504 |
| 59 | $C_2H_5$ | H | $(CH_3)_2CHCH_2$ | O | $n_D^{22}$ 1.4501 |
| 60 | $(CH_3)_2CH$ | H | $(CH_3)_2CHCH_2$ | O | $n_D^{22}$ 1.4497 |
| 61 | $CH_2$=$CHCH_2$ | H | $(CH_3)_2CHCH_2$ | O | $n_D^{22}$ 1.4635 |
| 62 | $ClCH$=$CHCH_2$ | H | $(CH_3)_2CHCH_2$ | O | 45–47 |
| 63 | $(CH_3)_2CHCH_2$ | H | $(CH_3)_2CHCH_2$ | O | $n_D^{22}$ 1.4491 |
| 64 | $C_2H_5$ | H | $CH_3(CH_2)_{16}$ | O | $n_D^{22}$ 1.4550 |
| 65 | $(CH_3)_2CH$ | H | $CH_3(CH_2)_{16}$ | O | $n_D^{22}$ 1.4528 |
| 66 | $CH_2$=$CHCH_2$ | H | $CH_3(CH_2)_{16}$ | O | $n_D^{22}$ 1.4633 |
| 67 | $ClCH$=$CHCH_2$ | H | $CH_3(CH_2)_{16}$ | O | 41–43 |

TABLE 1-continued $R^1-ON(R^2)-CO-CO-X-R^3$  IA

| Ex. No. | $R^1$ | $R^2$ | $R^3$ | X | mp (°C.) bp (°C./mbar) Refractive index $^1$H-NMR (δ in ppm)* |
|---|---|---|---|---|---|
| 68 | $CH_2=CHCH_2$ | H | $CH_3(CH_2)_3CH(C_2H_5)CH_2$ | O | $n_D^{22}$ 1.4651 |
| 69 | $(CH_3)_2CHCH_2$ | H | $CH_3(CH_2)_8$ | O | $n_D^{22}$ 1.4543 |
| 70 | $C_2H_5$ | H | $CH_3(CH_2)_8$ | O | $n_D^{22}$ 1.4562 |
| 71 | $CH_2=CHCH_2$ | H | $CH_3(CH_2)_8$ | O | 35–37 |
| 72 | $CH_2=CHCH_2$ | H | $CH_3(CH_2)_9$ | O | 36–38 |
| 73 | $CH_2=CHCH_2$ | H | $CH_3(CH_2)_{11}$ | O | 46–47 |
| 74 | $ClCH=CHCH_2$ | H | $CH_3(CH_2)_{11}$ | O | 61–64 |
| 75 | $C_2H_5$ | H | $CH_3(CH_2)_{15}$ | O | 61–62 |
| 76 | $(CH_3)_2CH$ | H | $CH_3(CH_2)_{15}$ | O | 68–70 |
| 77 | $CH_2=CHCH_2$ | H | $CH_3(CH_2)_{15}$ | O | 60–63 |
| 78 | $ClCH=CHCH_2$ | H | $CH_3(CH_2)_{15}$ | O | 75–77 |
| 79 | $(CH_3)_2CH$ | H | $CH_3(CH_2)_3CH(C_2H_5)CH_2$ | O | $n_D^{22}$ 1.4558 |
| 80 | $CH_2=C(CH_3)CH_2$ | H | $CH_3(CH_2)_3CH(C_2H_5)CH_2$ | O | $n_D^{22}$ 1.4668 |
| 81 | $(CH_3)_2CHCH_2$ | H | $CH_3(CH_2)_3CH(C_2H_5)CH_2$ | O | $n_D^{22}$ 1.4555 |
| 82 | $CH_3C(Cl)=CHCH_2$ | H | n-$C_3H_7$ | O | 2.16(s); 4.50(d); 4.64(d) |
| 83 | $HC\equiv C-CH_2$ | H | n-$C_3H_7$ | O | 2.64(s); 4.63(s) |
| 84 | 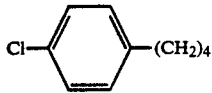 4-Cl-C$_6$H$_4$-(CH$_2$)$_4$ | H | n-$C_3H_7$ | O | 3.98(t); 4.28(t) |
| 85 | 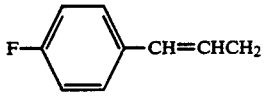 4-F-C$_6$H$_4$-CH=CHCH$_2$ | H | n-$C_3H_7$ | O | 6.45(d); 6.98(t) |
| 86 | 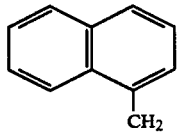 1-naphthyl-CH$_2$ | H | n-$C_3H_7$ | O | 5.64(s); 8.37(d) |
| 87 | 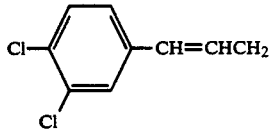 3,4-Cl$_2$-C$_6$H$_3$-CH=CHCH$_2$ | H | n-$C_3H_7$ | O | 6.42(d); 7.13(d) |
| 88 | 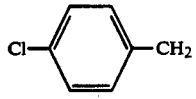 4-Cl-C$_6$H$_4$-CH$_2$ | H | n-$C_3H_7$ | O | 4.97(s); 7.32(m) |
| 89 | $(CH_3)_2C=CHCH_2C(CH_3)=CHCH_2$ | H | n-$C_3H_7$ | O | 4.27(t); 4.49(d) |
| 90 | 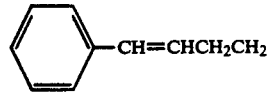 C$_6$H$_5$-CH=CHCH$_2$ | H | n-$C_3H_7$ | O | 4.03(t); 6.39(d) |
| 91 | 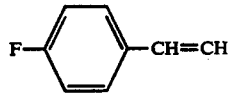 4-F-C$_6$H$_4$-CH=CH | H | n-$C_3H_7$ | O | 4.62(d); 6.61(d) |
| 92 | 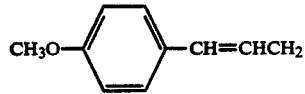 4-CH$_3$O-C$_6$H$_4$-CH=CHCH$_2$ | H | n-$C_3H_7$ | O | 3.81(s); 6.89(m) |
| 93 | 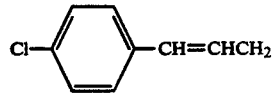 4-Cl-C$_6$H$_4$-CH=CHCH$_2$ | H | n-$C_3H_7$ | O | 6.45(d); 7.26(s) |

TABLE 1-continued

R$^1$—ON(R$^2$)—CO—CO—X—R$^3$   IA

| Ex. No. | R$^1$ | R$^2$ | R$^3$ | X | mp (°C.) bp. (°C./mbar) Refractive index $^1$H-NMR (δ in ppm)* |
|---|---|---|---|---|---|
| 94 | 3-Cl-C$_6$H$_4$-CH$_2$- | H | n-C$_3$H$_7$ | O | 4.29(t); 4.96(s) |
| 95 | 2-CH$_3$-C$_6$H$_4$-CH$_2$- | H | n-C$_3$H$_7$ | O | 2.45(s); 5.02(s) |
| 96 | 4-Cl-C$_6$H$_4$-CH=CH- | H | n-C$_3$H$_7$ | O | 4.63(d); 6.58(d) |
| 97 | C$_6$H$_5$-CH=CH- | H | n-C$_3$H$_7$ | O | 4.61(d); 6.61(m) |
| 98 | 3-CH$_3$-C$_6$H$_4$- | H | n-C$_3$H$_7$ | O | 2.35(s); 4.95(s) |
| 99 | 4-CH$_3$-C$_6$H$_4$- | H | n-C$_3$H$_7$ | O | 2.34(s); 4.92(s) |
| 100 | 4-CH$_3$-C$_6$H$_4$-CH$_2$CH=CH- | H | n-C$_3$H$_7$ | O | 2.31(s); 4.46(d) |
| 101 | C$_6$H$_5$-CH$_2$CH$_2$- | H | n-C$_3$H$_7$ | O | 3.98(t); 7.22(m) |
| 102 | C$_6$H$_5$-CH$_2$- | H | n-C$_3$H$_7$ | O | 4.25(m); 7.24(m) |
| 103 | C$_6$H$_5$-CH$_2$CH=CHCH$_2$- | H | n-C$_3$H$_7$ | O | 4.43(d); 5.70(m) |

USE EXAMPLES

The growth-regulating action of the compounds of the general formula IA is demonstrated in the following experiments.

The active ingredients were formulated
a) as a 0.1% strength solution in acetone, or
b) as a 10% strength emulsion in a mixture of 70 wt % of cyclohexanol, 20 wt % of Nekanil ® LN (Lutensol ® AP6, a spreader-sticker with an emulsifying and dispersing action based on ethoxylated alkylphenols) and 10 wt % of Emulphor ® EL (Emulan ® EL, an emulsifier based on ethoxylated fatty alcohols)
and diluted to the desired concentration with acetone in the case of a) and with water in the case of b).

The vessels employed were plastic flowerpots having a diameter of about 12.5 cm and a volume of about 500 cm$^3$ and were filled with a sandy loam containing about 3.0% humus. The seeds of the test plants were sown separately, according to species.

For the preemergence treatment, the formulated active ingredients were applied to the surface of the soil immediately after the seeds had been sown. The compounds were emulsified or suspended in water as vehicle, and sprayed through finely distributing nozzles. After the agents had been applied, the vessels were lightly sprinkler-irrigated to induce germination and growth. Transparent plastic covers were then placed on the vessels until the plants had taken root. The cover ensured uniform germination of the plants.

For the postemergence treatment, the plants were grown, depending on growth form, to a height of 3 to 15 cm before being treated with the compounds, suspended or emulsified in water.

The pots were set up in the greenhouse, heat-loving species at 20° to 35° C., and species from moderate climates at 10° to 25° C. The experiments were run for from 2 to 4 weeks. During this period the plants were tended and their reactions to the various treatments assessed.

The growth-regulating action observed was confirmed at the end of the experiment by measuring the growth height. The figures obtained were compared with the growth height of untreated plants.

The comparative agent used for assessing the growth-regulating action was N-(2-chloroethyl)-N,N,N-trimethylammonium chloride (Example A).

The plants used in the greenhouse experiments were: spring wheat ("Ralle" variety), spring barley ("Aramir" variety), rice ("Bahia" variety), grass ("Apache" variety), sunflowers ("Spanners Allzweck" variety), linseed and cotton ("Stoneville 825" variety).

On postemergence application of 0.4 mg/vessel, compounds 2, 17, 18, 20, 21, 23, 26, 30-33, 35, 38-40, 43 and 46 had a better action on spring wheat, compounds 2, 17, 18, 20-23, 25, 26, 28, 30-35, 37-40, 43-49 and 51 a better action on spring barley, and compounds 20, 26, 38, 43 and 45 a better action on rice, than prior art growth regulator A.

On postemergence application of 1.5 mg/vessel, compounds 20, 26 and 32 had a better action on cotton and compound 16 a better action on linseed than prior art growth regulator A.

On postemergence application of 6.0 mg/vessel, compounds 82 and 83 had a better action on spring wheat and spring barley, compound 20 had a better action on grass, and compounds 2, 16-18, 20-23, 25, 26, 28, 30-33, 35, 37-39, 43, 45-49, 51, 58, 82 and 83 had a better action on sunflowers than prior art growth regulator A.

The reduction in growth height was also accompanied by a deeper leaf coloration. The increased chlorophyll content is indicative of an increased rate of photosynthesis, making for bigger yields.

What we claim is:

1. Oxalylhydroxamic acid derivatives of the formula

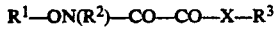    I, where the substituents have the following meanings:
X is oxygen or sulfur;
$R^1$ is
  $C_3$–$C_{18}$-alkenyl or $C_3$–$C_8$-alkynyl, where these groups may carry from one to five halogen atoms;
  monocyclic or polycyclic $C_3$–$C_{10}$-cycloalkyl or $C_3$–$C_{10}$-cycloalkylmethyl, where these rings may carry from one to three $C_1$–$C_4$-alkyl groups and/or one phenyl ring; or
  phenyl, where the aromatic radical may carry from one to five halogen atoms and/or from one to three of the following groups: nitro, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio and $C_1$–$C_4$-haloalkylthio;
$R^2$ is hydrogen, $C_1$–$C_4$-alkyl, $C_3$–$C_4$-alkenyl or benzyl, where the aromatic radical may carry from one to five halogen atoms and/or from one to three of the following groups: $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio and $C_1$–$C_4$-haloalkylthio;
$R^3$ is
  $C_1$–$C_{20}$-alkyl which may carry from one to five halogen atoms and/or from one to three of the following groups: cyano, $C_1$–$C_{10}$-alkoxy, $C_1$–$C_4$-haloalkoxy, $C_1$–$C_4$-alkylthio, $C_1$–$C_4$-haloalkylthio, $C_3$–$C_{10}$-cycloalkyl, $C_3$–$C_{10}$-cycloalkoxy, $C_3$–$C_{10}$-cycloalkylthio and $C_3$–$C_{12}$-alkenyloxy;
  $C_3$–$C_{18}$-alkenyl or $C_3$–$C_8$-alkynyl, where these groups may carry from one to five halogen atoms;
  monocyclic or polycyclic $C_3$–$C_{10}$-cycloalkyl which may carry from one to three $C_1$–$C_4$-alkyl groups;
  phenyl-$C_1$–$C_4$-alkyl or phenoxy-$C_1$–$C_4$-alkyl, where the aromatic radicals may carry from one to five halogen atoms and/or from one to three of the following groups: nitro, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio and $C_1$–$C_4$-haloalkylthio;
and agriculturally useful salts thereof.

2. Compounds of the formula I as set forth in claim 1, where $R^1$ is $C_3$–$C_{18}$-alkenyl or $C_3$–$C_8$-alkynyl, each of which may carry from one to five halogen atoms.

3. Compounds of the formula I as set forth in claim 1, where $R^3$ is one of the following radicals:
  $C_1$–$C_{20}$-alkyl, $C_3$–$C_{18}$-alkenyl or $C_3$–$C_8$-alkynyl, where these groups may carry from one to five halogen atoms, or
  monocyclic or polycyclic $C_3$–$C_{10}$-cycloalkyl or $C_3$–$C_{10}$-cycloalkylmethyl which may carry from one to three $C_1$–$C_4$-alkyl groups.

4. An agent for regulating the growth of plants and which contains an oxalylhydroxamic acid derivative of the formula I as set forth in claim 1, and inert additives.

5. A method of regulating the growth of crop plants, wherein the crop plants, their habitat and/or their seed are treated with a growth regulating active amount of an oxalylhydroxamic acid derivative of the formula IA

    IA, where the substituents have the following meanings:
X is oxygen or sulfur;
$R^1$ is
  $C_1$–$C_{20}$-alkyl, $C_3$–$C_{18}$-alkenyl or $C_3$–$C_8$-alkynyl, where these groups may carry from one to five halogen atoms;
  $C_2$–$C_8$-alkyl carrying a $C_1$–$C_{12}$-alkoxy group;
  monocyclic or polycyclic $C_3$–$C_{10}$-cycloalkyl or $C_3$–$C_{10}$-cycloalkylmethyl, where these rings may carry from one to three $C_1$–$C_4$-alkyl groups and/or one phenyl ring;
  phenyl or phenyl-$C_1$–$C_4$-alkyl, where the aromatic radicals may carry from one to five halogen atoms and/or from one to three of the following groups: nitro, $C_1$–$C_4$-alkyl, $C_1$–$C_4$-haloalkyl, $C_1$–$C_4$- alkoxy, $C_1$–$C_4$-haloalkoxy, $C_1$–$C_4$-alkylthio and $C_1$–$C_4$-haloalkylthio;

$R^2$ is hydrogen, $C_1$–$C_4$-alkyl, $C_3$–$C_4$-alkenyl or benzyl, where the aromatic radical may carry from one to five halogen atoms and from one to three of the following groups: $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio and $C_1$–$C_4$-haloalkylthio;

$R^3$ is $C_1$–$C_{20}$-alkyl which may carry from one to five halogen atoms and/or from one to three of the following groups: cyano, $C_1$–$C_{10}$-alkoxy, $C_1$–$C_4$-haloalkoxy, $C_1$–$C_4$-alkylthio, $C_1$–$C_4$-haloalkylthio, $C_3$–$C_{10}$-cycloalkyl, $C_3$–$C_{10}$-cycloalkoxy, $C_3$–$C_{10}$-cycloalkylthio and $C_3$–$C_{12}$-alkenyloxy;

$C_3$–$C_{18}$-alkenyl or $C_3$–$C_8$-alkynyl, where these groups may carry from one to five halogen atoms;

monocyclic or polycyclic $C_3$–$C_{10}$-cycloalkyl which may carry from one to three $C_1$–$C_4$-alkyl groups;

phenyl-$C_1$–$C_4$-alkyl or phenoxy-$C_1$–$C_4$-alkyl, where the aromatic radicals may carry from one to five halogen atoms and/or from one to three of following groups: nitro, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio and $C_1$–$C_4$-haloalkylthio.

* * * * *